(12) United States Patent
Raleigh

(10) Patent No.: US 6,569,669 B1
(45) Date of Patent: May 27, 2003

(54) HOST STRAIN FOR LOW UNINDUCED EXPRESSION OF FOREIGN RNA POLYMERASE GENES

(75) Inventor: Elisabeth A. Raleigh, Somerville, MA (US)

(73) Assignee: New England Biolabs, Inc., Beverly, MA (US)

( * ) Notice: Subject to any disclaimer, the term of this patent is extended or adjusted under 35 U.S.C. 154(b) by 0 days.

(21) Appl. No.: 09/689,359

(22) Filed: Oct. 12, 2000

(51) Int. Cl.[7] .................. C12P 21/06; C12N 15/09; C12N 1/20; C12N 15/74; C12N 15/76
(52) U.S. Cl. .................. 435/252.33; 435/69.1; 435/69.2; 435/471; 435/476; 435/478
(58) Field of Search .................. 435/69.1, 320.1, 435/471, 476, 478, 252.33, 69.2

(56) References Cited

U.S. PATENT DOCUMENTS 5,830,694 A * 11/1998 Studier et al.
6,165,749 A * 12/2000 Sagawa et al.

OTHER PUBLICATIONS

Studier, et al., Meth. Enzymol., 185:60–69 (1990).
Morris, et al., Gene 41:193–200 (1986).
Dubendorff and Studier, J. Mol. Biol. 219:45–59 (1991).
Maneewannakul, et al., Plasmid 31:300–307 (1994).
Munson, et al., Gene 144:59–62 (1994).
Andrews, et al., Gene 182:101–109 (1996).
Gilbert and Müller–Hill, Proc. Natl. Acad. Sci. USA 56:1891–1898 (1996).
Kennell and Riezman, J. Mol. Biol. 114:1–21 (1977).
Ausubel, et al., Current Protocols in Molecular Biology, John Wiley and Sons pp. 1.5–1.15, 13.4–13.6 and 9.9–9.14 (1999).
Yanisch–Perron, et al., Gene, 33:103–119 (1985).
Calos, Nature, 274:762–765 (1978).
Müller–Hill, et al., Proc. Natl. Acad. Sci. USA., 59:1259 (1968).
Hawley and McClure, Nucleic Acids Res. 11:2237–2255 (1983).
Angrand, et al., Nucleic Acids Res. 27:e16 (1999).
Payne, et al. J. Hum. Hypertens, 13:845–848 (1999).
Posfai, et al., J. Bacteriol. 179:4426–4428 :(1997).
Andrew et al. A tightly regulated high level expression vector that utilizes a thermosensitive lac repressor: production of the human T Cell receptor VB5.3 in *Escherichia coli* Gene 182 1996 101–109.*
Munson et al. ColE1–compatible vectors for high–leveln expression of cloned DNAs from the T7 promoter 1994 Elsevier Science B. V. 0378–1119.*
Szafranski et al. A new approach for containment og microorganisms: Dual control of streptavidin expression by antisense RNA and the T7 transcription system Pro Natl acad Scri USA vol. 94 pp. 1059–1063 Feb. 1997.*
Studier et al. Use of T7 RNA Polymerase to Direct Expression of Cloned Genes Methods in Enzymolgy vol. 185.*

* cited by examiner

Primary Examiner—Remy Yucel
Assistant Examiner—Konstantina Katcheves
(74) Attorney, Agent, or Firm—Gregory D. Williams; Harriet M. Strimpel

(57) ABSTRACT

The present invention relates to host cells suitable for expressing genes under the direction of foreign RNA polymerases and to providing very low levels of expression of such genes and RNA polymerases in the absence of induction.

5 Claims, 2 Drawing Sheets

US 6,569,669 B1

HOST STRAIN FOR LOW UNINDUCED EXPRESSION OF FOREIGN RNA POLYMERASE GENES

BACKGROUND OF THE INVENTION

Expression of proteins toxic to the cell requires that the construct (expression vector) used for final production be made and stored under conditions where the toxic protein is not expressed or is expressed at extremely low levels. It is convenient for this purpose to use expression signals (especially transcriptional promoters) that are not recognized by the cells used during construction (Studier, et al., *Meth. Enzymol.*, 185:60–89 (1990); U.S. Pat. No. 4,952,496 (1990), Studier et al., "Cloning and expression of the gene for bacteriophage T7 RNA polymerase").

Expression is then accomplished by introducing the expression vector into a special cell line that makes a foreign RNA polymerase that does recognize the expression signal (promoter). Foreign RNA polymerases that recognize highly specific promoter sequences distinct from those recognized by bacteria include those encoded by T7-like phages and may be selected from the group consisting of *Escherichia coli* phages T3, .phi.I, .phi.II, W31, H, Y, A1122,cro, C21, C22 and C23; Pseudomonas putida phage gh-1; *Salmonella typhimurium* phage Sp6; *Serratia marcescens* phage IV; Citrobacter phage VIIII; and Klebsiella phage number 11. The RNA polymerase of T3 has been used-this way (Morris, et al., *Gene*, 41:193–200 (1986)). In principle, such foreign RNA polymerases could include those of Archaea or Eukaryotes. Such specialized bacteriophage RNA polymerases have also been used in eukaryotes as well (U.S. Pat. No. 5,550,035, Moss et al, "Prokaryotic expression in eukaryotic cells" (1996)).

Further, it is convenient to provide for regulation of the expression and activity of this foreign RNA polymerase, (Dubendorff and Studier, *J Mol Biol*, 219:45–59 (1991)). This is done in common cases in two ways: by providing a binding site (operator) for a transcriptional repressor as part of the expression signals for the foreign RNA polymerase gene itself; and by providing additional operators as part of the expression signals for the gene of interest. In common examples and in the present invention, the foreign RNA polymerase used is that of bacteriophage T7, the transcriptional regulator used is the LacI repressor, and the operator is the lac operator.

Accordingly, commonly used strains, e.g. BL21(DE3) and ER2566, provide a chromosomal copy of the lacI gene to facilitate negative regulation of expression of the T7 RNA polymerase before introduction of the plasmid vector carrying the gene of interest. In addition, to provide sufficient LacI to also repress copies of the T7 promoter carried on the plasmid vector itself, many such expression vectors provide further copies of the lacI gene (e.g. (Maneewannakul, et al., *Plasmid*, 31:300–7 (1994), Munson, et al., *Gene*, 144:59–62 (1994), Andrews, et al., *Gene*, 182:101–9 (1996)).

SUMMARY OF THE INVENTION

The invention relates to regulated expression of toxic genes by cells that use a foreign RNA polymerase to transcribe the gene for the toxic product. Specifically, the invention relates to provision of high levels of a negative. regulator of the expression of the foreign RNA polymerase or of the toxic gene or both, which high level of negative regulator is established in the cell before the introduction of the toxic gene.

In one preferred embodiment, the present invention provides an expression strain carrying a copy of the T7 RNA polyrderase gene together with a copy of the wild type lacI gene similar to other such strains available, but with the additional provision of further copies of the lacI gene with a mutated promoter such that 10-fold higher levels of the repressor protein are expressed than in the standard host.

Chromosomally encoded genetic elements in the typical situation (top) are present in a single copy per chromosome. The lacI gene is typically expressed from the wild type promoter pLacI, which is recognized by the vegetative *E. coli* RNA polymerase (EcRNAP). Transcription from this promoter is unregulated. The gene for the foreign RNAP, in this case that originating in bacteriophage T7 (T7RNAP), is expressed from the heterologous promoter pLac, also recognized by the EcRNAP. One or more copies of the LacI binding site, designated the lac operator (lacO) provides a site for regulation of transcription by binding of the LacI protein; this binding prevents EcRNAP from transcribing the gene. Before introduction of the vector bearing the gene of interest, these are the only genetic elements present that are relevant to the expression system.

Vector-borne genetic elements (bottom) are typically present in many copies but only one copy is shown for clarity. The vector is usually a plasmid but in some cases is a bacteriophage. The vector-borne genetic elements are introduced by transformation or infection into cells with the chromosomal components already present. Additional copies of the lacI gene are commonly provided on the vector, also commonly expressed from the wild type pLacI and read by EcRNAP. The gene of interest is expressed from a promoter recognized by the foreign RNA polymerase, here the T7 RNA polymerase promoter (pT7). One or more copies of lacO in the vicinity of pT7 provides a site for regulation of transcription of the gene of interest, also by binding of the LacI protein; this binding prevents T7 RNAP from transcribing the gene. Expression of the T7 RNAP and the gene of interest will be low when LacI is able to bind to lacO (the uninduced state). Expression will be high when LacI is unable to bind to lacO; this occurs when inducer (usually isopropyl β-D thiogalactoside, IPTG) is added, since binding of IPTG by the LacI protein induces a conformational change that inactivates binding (not shown).

Figure 2A:
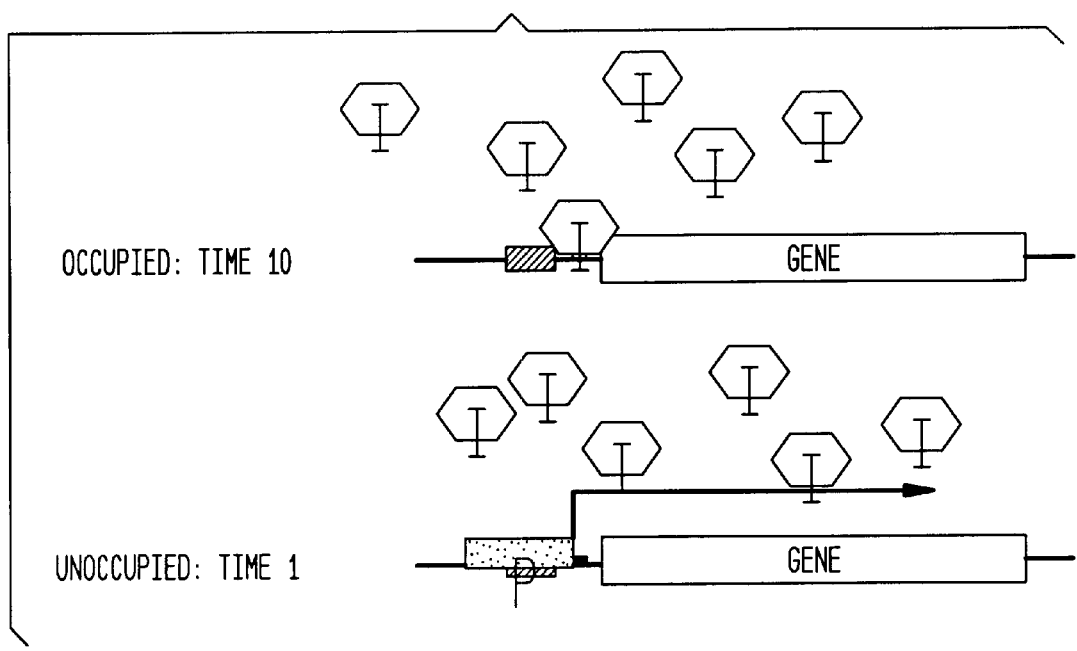
Figure 2B:
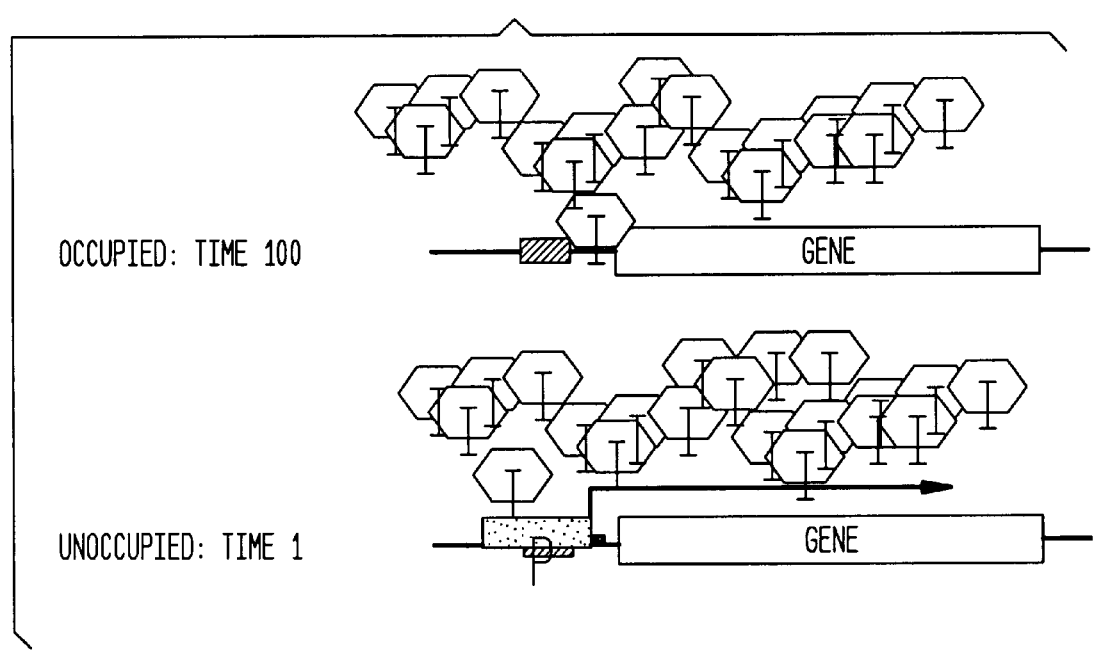

FIG. 2—Promoter occupancy with wild type LacI levels, uninduced condition.

Figure 1:
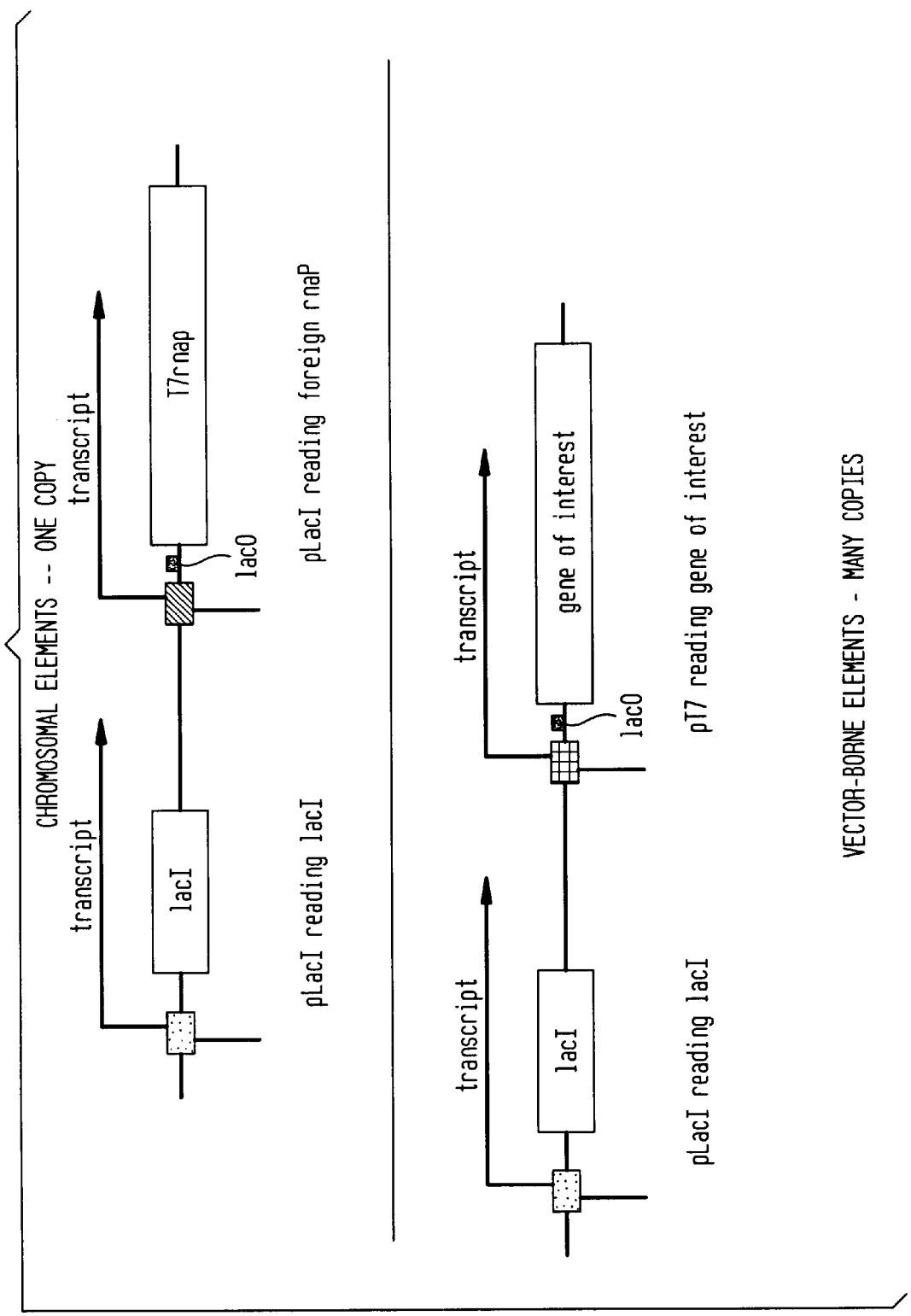
FIG. 1—Genetic elements of the condition of interest Open boxes: protein-encoding genes as labeled; Shaded boxes: DNA sequence elements comprising the regulatory sequences—stippled boxes, pLacI; filled box, pLacZYA; hatched box, pT7; shaded boxes, lacO; and Arrows: direction of transcription from illustrated promoters.

Genetic elements as in FIG. 1;

Hexagons: LacI protein; and

Stippled rectangle: foreign RNA polymerase.

Under uninduced conditions, an equilibrium is established between the molecules of LacI free in the cytoplasm and those bound to lacO, so that the operator is unoccupied some of the time. This time is determined by the concentration of LacI molecules in the cell. In turn, the amount of time that lacO is occupied by LacI determines the amount of time available for RNAP to bind to the promoter and begin transcription.

Panel A: with wild type levels of LacI the time the promoter is unoccupied (and available for RNAP binding) is arbitrarily illustrated as one-tenth the amount of time the amount of time the promoter is occupied. Panel B: with levels of LacI ten times higher than wild type, the time the promoter is unoccupied (and available for RNAP binding) is lowered by ten-fold, illustrated as one-one hundredth the amount of time it is occupied.

DETAILED DESCRIPTION OF THE INVENTION

It may occur that the preexisting level of the foreign RNA polymerase is too high, in cells that contain only a single copy of the wild type regulator gene To appreciate this, consider the common situation in which the negative regulator is LacI and the foreign RNA polymerase is the T7 RNA polymerase. The genetic elements of this system are illustrated in FIG. 1.

The resident chromosomal copy of lacI, which expresses the negative regulator of foreign RNA polymerase synthesis, is made at a level of approximately 10 molecules per cell (Gilbert and Müller-Hill, *Proc. Natl. Acad. Sci. USA*, 56:1891–1898 (1966)). One lac operator is present in the cell. Some repressor molecules bind to this operator, while others (the free pool) are present elsewhere in the cell. Those that occupy the promoter prevent expression of the foreign RNA polymerase gene.

Although repression drastically reduces expression from promoters regulated by this system, expression is not completely eliminated. In the case of the wild type lac operon, the level of uninduced transcription is about one transcript per cell (Kennell and Riezman, *J Mol Biol*, 114:1–21 (1977)), and lac-driven transcription in this case is likely to be similar. This occurs because repression is an equilibrium state: the bound molecules occasionally come off the operator, and others from the pool of free molecules replace them (FIG. 2). A particular ratio of bound to unbound molecules is thus established, which determines the amount of time in which the operator is unoccupied. During this time, the *E. coli* RNA polymerase may bind to the promoter, and transcribe the gene for the foreign RNA polymerase, which transcript can then be translated.

Translation of even a single transcript can give rise to significant levels of protein product. For example, about 40 molecules of β-galactosidase are made per transcript, although this number does not apply to the T7 RNA polymerase gene transcript in a straightforward way. Even if the number of translation products were lower, some molecules of foreign RNA polymerase may already be present in the uninduced cells before introduction of the expression vector.

Furthermore, the resulting translation products may be divided among the daughter cells upon division, so even cells that did not themselves transcribe and translate the foreign RNA polymerase gene may nevertheless contain some molecules of the product. This level can result in some expression of the potentially toxic target gene upon introduction even in the absence of induction.

A further effect can exacerbate the problem of preexisting foreign RNA polymerase molecules. A change in the ratio between the number of operators and the number of repressor molecules can change the amount of time available for expression of the foreign RNA polymerase gene, or the potentially toxic target gene, or both. This effect can be called operator titration, and applies to most instances of foreign RNA polymerase-dependent expression systems.

Operator titration can occur when the negative regulator used to repress expression of the foreign RNA polymerase is also used to repress expression of the target gene. When the expression vector (carrying the gene for the negative regulator, the operator site at which the negative regulator acts, and the gene to be expressed) is first introduced into the cell, additional copies of the operator will be bound by the preexisting free pool of repressor molecules, changing the time of occupancy of the operator controlling foreign RNA polymerase and toxic target gene synthesis. Escape synthesis of the foreign RNA polymerase and the toxic target gene is expected even in the absence of induction. This will occur if the number of copies of the operator, present on the plasmid, increases faster than the number of copies of the LacI repressor. This is likely, since DNA replication occurs rapidly, while transcription and translation of the LacI gene occur more slowly. A new balanced ratio of repressor molecules and operator molecules will eventually be achieved. This balance will be established when the steady state copy number of the vector has been reached, and the steady state level of 10 molecules of repressor per copy of lacI has been established. Some level of foreign RNA polymerase may have already been present as described above; but an even higher level will now be present due to expression during the establishment phase, and this pool of foreign RNA polymerase can express the toxic gene at a low level. Thus, there may be a race between expression of the negative regulator and expression of the toxic gene.

The preexisting level of the transcriptional regulator can be made to be higher however, which should result in increased operator occupancy, reduced availability of the promoter, and in reduction of both preexisting levels of the foreign RNAP and expression during the establishment phase after introduction of the expression vector. There are several ways to do this. For example, another vector carrying the wild type gene for the regulator in multiple copies (without additional operators for the regulator to bind to) can be established in the cell before introduction of the expression vector. For example, the gene for the regulator could be cloned onto vectors derived from λdv, pMB9, pMB1, colE1, pACYC184, pACYC177, p15A, pSC101, pUC19, or derivatives of these or of similar plasmids, or (in eukaryotic cells) of eukaryotic plasmid-like entities, such as 2-micron circle-derived plasmids of yeast, retroviral-derived vectors, vectors derived from adenovirus or SV40 or adeno-associated virus (AAV) in mammalian cells (Ausubel, et al., 1999). Another way to do this, and the one we chose, is to introduce a low-copy vector carrying a transcriptional overproducer of the regulator. This vector (F'lacI$^q$; (Yanisch-Perron, et al., *Gene*, 33:103–119 (1985)) expresses LacI of wild type sequence but at a 10–50 fold higher level (Calos, *Nature*, 274:762–5 (1978), Müller-Hill, et al., *Proc. Natl. Acad. Sci. USA.*, 59:1259 (1968)). A third way to do this would be to provide a heterologous promoter for the chromosomal copy of the lacI gene, one that also overproduces the LacI repressor. Promoters that might be used for this purpose include pOUT of Tn10, pHis, pHH104, pCAT, pBla, or unregulated versions of controllable promoters such as pL, pR, pAra, pTrp, pTet or pGal (see e.g. (Hawley and McClure, *Nucleic Acids Res*, 11:2237–55 (1983))); or, in eukaryotes, pCMV, pSV40, an LTR promoter or others (Ausubel, et al., 1999). These promoters could be introduced by restriction-enzyme mediated cloning strategies, by PCR-based cloning strategies, or by allele replacement methods (e.g. (Angrand, et al., *Nucleic Acids Res*, 27:e16 (1999), Payne, et al., *J Hum Hypertens*, 13:845–8 (1999), Posfai, et al., *J Bacteriol*, 179:4426–8 (1997)).

However achieved, this higher level of expression provides two things: an altered balance point in the expression of foreign RNA polymerase before introduction of the expression vector, with less expression expected; and a change in the dynamics of expression upon introduction of the vector expressing the desired gene, with less expression of either the foreign RNA polymerase or the toxic gene, in the absence of induction.

The present invention is further illustrated by the following Example. This Example is provided to aid in the understanding of the invention and is not construed as a limitation thereof.

The references cited above and below are herein incorporated by reference.

EXAMPLE I

ER2833 (a *E. coli* B derivative expressing T7 RNAP and containing lacI$^q$) was constructed by mating the recipient strain ER2566 F- fhuA2 [lon] ompT lacZ::T7 gene1 gal sulA11 Δ(mcrC-mrr)114::IS10 R(mcr-73::miniTn10—TetS)2 R(zgb-210::Tn10—TetS) endA1 [dcm] with the donor strain ER2353 F' proA+B+lacIq Δ(lacZ)M15 zzf::Tn10 (TetR)/fhuA2 Δ(argF-lac)U169 glnV44 e14-trp-31 his-1 rpsL104 xyl-7 mtl-2 metB1 ΔmcrC-mrr)114::IS10 and selecting on minimal tetracycline plates. Eight resulting colonies were purified once on minimal tetracycline and once on RB. All isolates were tested for the presence of the T7 RNA polymerase gene inserted into lacZ by colony PCR, using primers A and B. Primer A (5' primer) binds in the middle of lacI (5'GCATCTGGTCGCATTGGGTCACCAG 3'(SEQ ID NO:1)). Primer B (NEB#S1247S) binds to pBR322 upstream of the BamH I in the tetracycline resistance gene; there is a short stretch of pBR322 sequence downstream of the T7RNAP gene in the chromosomal construction. The sequence of B is 5'TACTTGGAGCCACTATCGACTACGCGATCA 3' (SEQ ID NO:2). The PCR product expected is 3896 bp and includes about half of lacI, the lacUV5 promoter and the entire T7RNAP sequence. Isolate #5 consistently showed a PCR product of the correct size in 3 separate PCR experiments on 3 different days (trying different methods of sample preparation). Other isolates showed less consistent PCR results, but all isolates behaved as expected in other tests (TetR, KanS, Gal-). All isolates were also Lac+, presumably because of complementation with the lac sequence present on the F'. Isolate #5 was designated ER2833. Note that standard means to test for the presence of the T7 RNA polymerase gene, thus verifying the construction, rest on the ability of the cell to complement a mutation in the gene present on the bacteriophage T7, enabling the mutant phage to form plaques. This method will not work in the present example, because T7 is a female-specific phage and will not form plaques on strains containing F or its derivatives.

A similar strain in a different strain background (a derivative of *E. coli* K-12) was contructed by the same method. ER2744 (F- fhuA2 glnV44 e14- rfbD1? relA1? endA1 spoT1? thi-1 Δ(mcrC-mrr)114::IS10 lacZ::T7 gene1) was mated with ER2353; TetR, prototrophic recombinants were selected; isolates were tested for yield PCR products; and the resulting strain was designated ER2848. A sample of ER2848 was deposited under the terms and conditions of the Budapest Treaty with the American Type Culture Collection on Oct. 12, 2000 and received ATCC Accession No. PTA-2597.

ER2833 was shown to be capable of stably supporting a T7-driven expression plasmid in which the toxic gene expressed is the MseI restriction endonuclease, while its isogenic parent lacking the lacI$^q$ allele was unable to do so. See, e.g., U.S. patent application Ser. No. 09/689,343, filed Oct. 12, 2000. A sample of ER2833 was deposited under the terms and conditions of the Budapest Treaty with the American Type Culture Collection on Oct. 12, 2000 and received ATCC Accession No. PTA-2596.

What is claimed is:

1. A host cell containing a negative regulator of transcription of a gene encoding a foreign RNA polymerase together with the gene for a regulated foreign RNA polymerase wherein the negative regulator is expressed at a level of greater than about 10 molecules per cell, wherein the negative regulator is lac I and wherein the level of the negative regulator is achieved by introduction of the laI$^q$ allele.

2. The host cell of claim 1, in which the lacI$^q$ allele is introduced on an F' plasmid.

3. A host cell of claim 1, in which the host is a strain of *E. coli*.

4. The host cell of claim 3, in which the strain is ER2833.

5. The host cell of claim 3, in which the strain is ER2848.

* * * * *

```
                       SEQUENCE LISTING

<160> NUMBER OF SEQ ID NOS:  2

<210> SEQ ID NO 1
<211> LENGTH: 25
<212> TYPE: DNA
<213> ORGANISM: Escherichia coli

<400> SEQUENCE: 1
gcatctggtc gcattgggtc accag                                        25

<210> SEQ ID NO 2
<211> LENGTH: 30
<212> TYPE: DNA
<213> ORGANISM: Escherichia coli

<400> SEQUENCE: 2
tacttggagc cactatcgac tacgcgatca                                   30
```